United States Patent

Foricher et al.

Patent Number: 5,910,606
Date of Patent: Jun. 8, 1999

[54] PROCESS FOR MAKING α,β-UNSATURATED CARBOXYLIC ACIDS

[75] Inventors: Joseph Foricher, Mulhouse, France; Rudolf Schmid, Arlesheim, Switzerland

[73] Assignee: Hoffmann-La Roche Inc., Nutley, N.J.

[21] Appl. No.: 08/780,952

[22] Filed: Jan. 10, 1997

[30] Foreign Application Priority Data

Jan. 31, 1996 [CH] Switzerland ............... 247/96

[51] Int. Cl.⁶ .................................. C07C 63/64
[52] U.S. Cl. .......................... 562/495; 562/470
[58] Field of Search ............................. 562/495

[56] References Cited

U.S. PATENT DOCUMENTS

| | | | |
|---|---|---|---|
| 4,409,397 | 10/1983 | Paxson | 562/496 |
| 4,808,605 | 2/1989 | Branca et al. | 514/394 |
| 5,120,759 | 6/1992 | Hengartner et al. | |

FOREIGN PATENT DOCUMENTS

| | | |
|---|---|---|
| 268 148 | 5/1988 | European Pat. Off. |
| 272 787 | 6/1988 | European Pat. Off. |
| 275 354 | 7/1988 | European Pat. Off. |
| 388 739 | 9/1990 | European Pat. Off. |
| 667 350 | 8/1995 | European Pat. Off. |
| 673 911 | 9/1995 | European Pat. Off. |
| 960 814 | 3/1997 | Germany. |
| 64-9952 | 1/1989 | Japan. |

OTHER PUBLICATIONS

Derwent Abstract No. 89–057709, JP 960 16078, Feb. 21, 1996.

Hayashi, T., et al., *J. Am. Chem. Soc.*, 109:7876–7878 (1987).

Ohta, T., et al., *J. Org. Chem.*, 52:3174–3176 (1987).

Schmid, R., et al., *Pure & Appl. Chem.*, 68(1):131–138 (1996).

Takemoto, I., et al., *Biosci. Biotech. Biochem.*, 58(11):2071–2072 (1994).

*Chemical Abstracts*, 53:14939b. (1957).

*Primary Examiner*—Paul J. Killos
*Attorney, Agent, or Firm*—George W. Johnston; Patricia S. Rocha-Tramaloni; Alan P. Kass

[57] ABSTRACT

α, β-Unsaturated acids of the formula

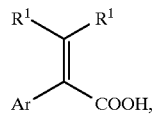

I wherein $R^1$ signifies $C_1$–$C_5$-alkyl and Ar signifies an aryl group which is optionally substituted by one or more substituents selected from the group consisting of halogen, phenyl, $C_1$–$C_5$-alkyl, $C_1$–$C_5$-alkoxy, perfluorinated $C_1$–$C_5$-alkyl or perfluorinated $C_1$–$C_5$-alkoxy can be obtained from new or known compounds of the formula

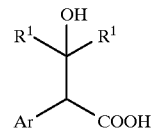

III

Compounds I can be converted by asymmetric hydrogenation into corresponding optically active saturated acids.

11 Claims, No Drawings

PROCESS FOR MAKING α,β-UNSATURATED CARBOXYLIC ACIDS

The invention is concerned with a novel process for making α,β-unsaturated acids of formula I

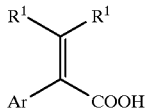

I wherein $R^1$ signifies $C_1$–$C_5$-alkyl; and Ar signifies an aryl group which is optionally substituted by one or more substituents selected from the group consisting of halogen, phenyl, $C_1$–$C_5$-alkyl, $C_1$–$C_5$-alkoxy, perfluorinated $C_1$–$C_5$-alkyl and perfluorinated $C_1$–$C_5$-alkoxy.

The process in accordance with the invention comprises dehydrating a compound of formula

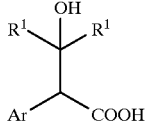

III wherein $R^1$ and Ar have the significances given above, in the presence of a strong acid and, if desired, a solubilizer at a temperature of 0–40° C., and recovering the compound of formula I.

The compounds of formula I are known. See for example U.S. Pat. No. 4,409,397. The compounds of the present invention are important intermediates for making pharmacologically usable products, such as e.g. the calcium antagonist [1S,2S]-2-[2-[[3-(2-benzimidazolyl)propyl] methylamino]ethyl]-6-fluoro-1,2,3,4-tetrahydro-1-isopropyl-2-naphthylmethoxyacetate dihydrochloride (mibefradil), or for making other useful materials, such as pesticides. Thus, compounds of formula I can be converted directly by asymmetric hydrogenation in the presence of an optically active diphosphine complex with a transition metal of Group VIII, such as, for example, rhodium or ruthenium, as the catalyst into the optically active acids of formula II

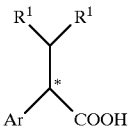

II wherein $R^1$ and Ar have the significances given above.

The process in accordance with the invention substantially simplifies and improves the making of compounds of formula I and consequently provides a direct access to the compounds of formula II, which hitherto have been preferably isolated via a racemate resolution. The preparation of compounds of formula I by the dehydration of corresponding hydroxy compounds has been described in the literature. Thus, for example, it is mentioned in U.S. Pat. No. 4,409, 397 that the dehydration can be realized in the presence of p-toluenesulphonic acid or $KHSO_4$.

The acids which are recommended in U.S. Pat. No. 4,409,397 do indeed work for the dehydration of compounds of formula III, but give only low yields of compounds of formula I because of concurrent dehydration to isomeric acids of formula IV and dehydrating decarboxylation to compounds of formula V, with the latter taking place as the main reaction (Scheme 1).

Scheme 1

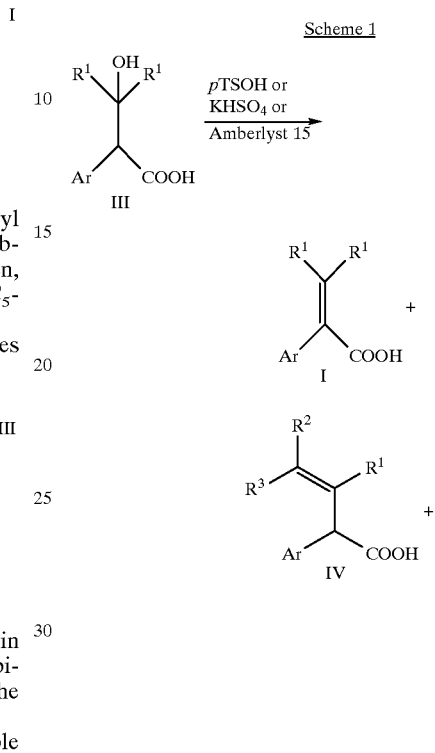

wherein $R^1$ and Ar have the significances given above; and $R^2$ and $R^3$ each independently signify hydrogen or straight-chain ($C_1$–$C_4$)-alkyl, with groups $R^2$ and $R^3$ together having a maximum of 4 carbon atoms.

An acid-catalyzed dehydration to the ester stage with subsequent saponification can be carried out in order to avoid these concurrent reactions, but in this case two additional steps are required.

Surprisingly, it has now been found that very strong acids such as conc. sulphuric acid ($H_2SO_4$) or polyphosphoric acid bring about the direct dehydration of compounds of formula III very efficiently under very mild conditions at temperatures of from about 0 to about 40° C., preferably at temperatures of from about 20 to about 25°. Under these conditions, the dehydrating carboxylation to compounds of formula V and the formation of isomeric acids of formula IV are suppressed. Thus, for example, in the dehydration with conc. $H_2SO_4$ pure unsaturated acids of formula I are obtained in up to 99% yield. In this reaction the sulphuric acid functions not only as an acid, but also as the water-binding agent and solvent. A further advantage is that the reaction can be carried out at a very high concentration, e.g. using 2–2.5 parts conc. $H_2SO_4$/1 part hydroxy acid of formula III. If the hydroxy acid of formula III is used in crystalline form, then it is advantageous additionally to use a solubilizer which also has a certain dissolving power for $H_2SO_4$, such as, for example, $CH_2Cl_2$, dioxan or acetic acid, preferably $CH_2Cl_2$.

The dehydration of compounds of formula III can be carried out in a similar manner using polyphosphoric acid, likewise under mild conditions at temperatures of from about 0 to about 40° C., preferably from about 20 to about 35° C. However, other strong acids, such as, for example, HCL, HBr, HI, $H_3PO_4$ and HCOOH, do not give any reaction under mild conditions and the mixtures referred to above result at elevated temperatures.

The elegant dehydration using conc. $H_2SO_4$ accordingly provides an extremely advantageous, short process for making the unsaturated acids of formula I. These are accordingly obtained starting from arylacetic acids in a chemical two-stage (technically one-stage) process in up to 95% overall yield. An additional advantage of this synthesis is that the unsaturated acids of formula I are obtained in a very high purity, which is very advantageous for the subsequent asymmetric hydrogenation.

The terms used herein are defined below: "$C_1-C_5$-alkyl" signifies in the scope of the present invention methyl, ethyl, propyl, butyl, pentyl, i-propyl, 2-butyl, 2-pentyl and the like; "$C_1-C_5$-alkoxy" embraces groups in which the alkyl residue has the significances given earlier such as, for example, methoxy, ethoxy, propoxy, isopropoxy, 2-butyloxy, 2-pentyloxy, and the like; "perfluorinated $C_1-C_5$-alkyl" and "perfluorinated $C_1-C_5$-alkoxy" signify in the scope of the present invention trifluoromethyl, pentafluoroethyl perfluoropropyl, perfluorobutyl, perfluoropentyl, perfluoro-i-propyl, perfluoro-2-butyl, perfluoro-t-butyl, perfluoro-2-pentyl, trifluoromethoxy, pentafluoroethoxy, perfluoropropyloxy, perfluorobutyloxy, perfluoropentyloxy, perfluoro-i-propyloxy, perfluoro-2-butyloxy or perfluoro-2-pentyloxy; "an aryl group which is optionally substituted by one or more substituents selected from the group consisting of halogen, phenyl, $C_1-C_5$-alkyl, $C_1-C_5$-alkoxy perfluorinated $C_1-C_5$-alkyl and perfluorinated $C_1-C_5$-alkoxy" embraces in the scope of the present invention phenyl, phenyl which is fluorinated, chlorinated, alkylated and/or alkoxylated in the o-, m- and/or p-position, such as, for example, o-fluoro, m-fluoro, p-fluoro-, o-chloro-, m-chloro-, p-chloro-, p-bromo-, p-methyl-, p-methoxy-, p-$CF_3O$-phenyl and the like, as well as 1- or 2-napthyl which optionally can be mono- or multiply-substituted with halogen, $C_1-C_5$-alkyl or $C_1-C_5$-alkoxy, such as, for example, 2-naphthyl which is fluorinated, chlorinated, brominated, alkylated and/alkoxylated in the 6-position.

Methyl and ethyl are especially preferred groups $R^1$. Phenyl groups which are substituted with fluorine, chlorine, bromine, methyl, methoxy or trifluoromethoxy, especially in the p-position, are particularly preferred aryl groups Ar.

The compounds of the formula

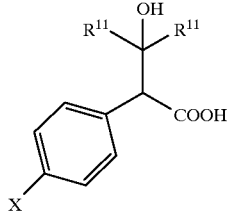

IIIa wherein $R^{11}$ signifies methyl or ethyl; and X signifies fluorine, chlorine or bromine,
are novel and are also an object of the invention.

The compounds of formula III and accordingly also the compounds of formula III can be prepared in a manner known per se starting from the corresponding arylacetic acids of formula VI. See Scheme 2. The preparation comprises, for example, the conversion of the corresponding arylacetic acids into the di-anions using 2 equivalents of a strong base and subsequent reaction with acetone. Strong bases which come into consideration are lithium and sodium amides, especially lithium dialkylamides, organolithium compounds or organomagnesium compounds, especially Grignard reagents. The Grignard reagents (RMgX, X=Cl, Br) especially MeMgCL, EtMgCl or iPropMgCL, are preferred on economical grounds. If desired, 1 equivalent of the strong base can also be replaced by NaH for the formation of the Na carboxylate or an alkali or alkaline earth salt of the acid can be used directly in order to save 1 equivalent of the strong base.

Where desired, the hydroxy acids of formula III can be isolated in pure form and crystallized; they are, however, advantageously subjected to the dehydration directly as the oily crude product.

Scheme 2

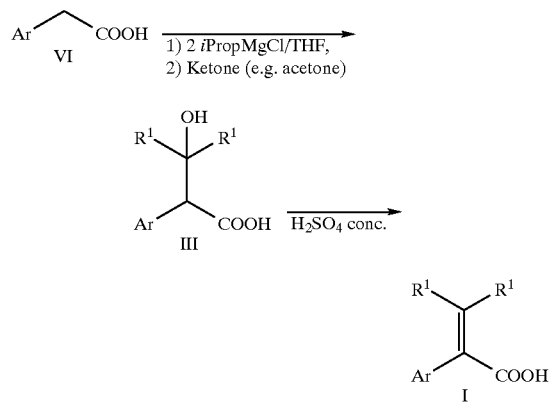

wherein $R^1$ and Ar have the significances given above.

An object of the present invention is to make the optically active acid of formula II

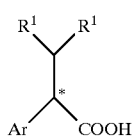

II by first dehydrating a compound of formula III

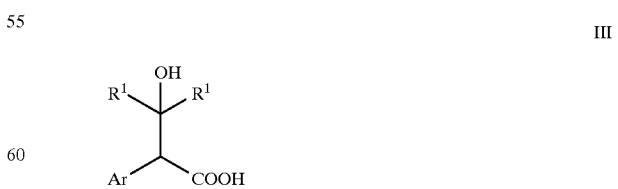

III in the presence of a strong acid selected from concentrated sulphuric acid or correlated polyphosphoric acid to form a compound of formula I

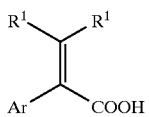

and then by enantioselectively hydrogenating the compound of formula I in the presence of an optically active ruthenium diphosphine complex to form a compound of formula IIa, and then recovering the compound of formula II. $R^1$ and Ar are as defined above.

A further object of the present invention is making the optically active acid of the formula IIb

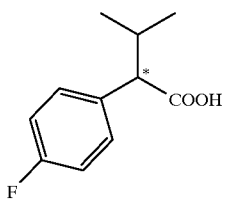

by the enantioselective hydrogenation of the compound of the formula

Ib

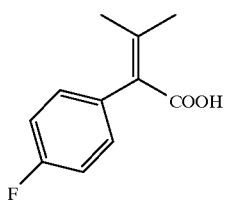

in the presence of an optically active ruthenium diphosphine complex, e.g. a ruthenium (R)-(6,6'-dimethylbiphenyl-2,2'-diyl)-bis(diphenylphosphine), a ruthenium (R)-(6,6'-dimethoxybiphenyl-2,2'-diyl)bis(diphenylphosphine) or a ruthenium [(R)-1-{(1S,2R)-1', 2-bis-diphenylphosphanyl-ferrocenyl}-ethyl]-methyl-(2-piperidin-1 -yl-ethyl)-amine complex as the catalyst, and then recovering the compound of formula IIb with compound Ib being made by dehydration of the compound of formula IIIb.

The compound (S)-2-(p-fluorophenyl)-3-methyl-butyric acid is converted using methylene chloride, thionyl chloride, aluminum trichloride and ethylene into 6-fluoro-1,2,3,4-tetrahydro-1-isopropyl-2-naphthalenone. This is then converted using tert.butyl acetate into the corresponding tetrahydronaphthalene hydroxyester and the latter is converted using benzimidazolylpropylamine in a known manner according to EP-B-0 268 148 into [1S,2S]-2-[2-[[3-(2-benzimidazoiyl)propyl]methylamino]ethyl]-6-fiuoro-1,2,3,4-tetrahydro-1-isopropyl-2-naphthylmethoxyacetate dihydrochloride (mibefradil) and then recovering the same.

The following Examples are intended to illustrate the present invention in more detail, but they do not in any manner represent a limitation. The abbreviations used in the Examples have the following significance:

(R)-BIPHEMP=(R)-(6,6'-Dimethylbiphenyl-2,2'-diyl)bis (diphenylphosphine)

(R)-MeOBIPHEP=(R)-(6,6'-Dimethoxybiphenyl-2,2'-diyl)bis (diphenylphosphine)

(R,S)-BPPFA-EPIP=[(R)-1-{(1S,2R)-1', 2-Bis-diphenylphos- phanyl-ferrocenyl}-ethyl]-methyl-(2-piperidin-1-yl-ethyl)-amine OAc=Acetate COD=1,5-Cyclooctadiene RT=Room temperature All temperatures are in degrees Celsius unless otherwise stated.

EXAMPLE 1

Preparation of 2-(p-fluorophenyl)-3-methylcrotonic acid (without isolation of the hydroxy acid)

a) 24.3 g (1.00 mol) of magnesium shavings were suspended in 50 ml of tetrahydrofuran under argon and while stirring in a 1.5 l four-necked sulphonation flask fitted with a reflux condenser, mechanical stirrer, 500 ml dropping funnel, thermometer and a device for inert gasification. After the dropwise addition of 0.5 ml of 1,2-dibromoethane, a solution of 86.4 g (1.10 mol) of isopropyl chloride in 225 ml of tetrahydrofuran was added dropwise within 90 minutes, with the reaction temperature being held at about 30°. The resulting dark grey suspension was stirred at RT for a further 18 hours. Then, a solution of 73.0 g (0.473 mol) of p-fluorophenylacetic acid in 150 ml of tetrahydrofuran was added dropwise to the mixture within 90 minutes while maintaining the temperature at about 25° and thereafter the suspension was heated to 35–40° and stirred at this temperature for a further 1 hour. After cooling 30.0 g (0.516 mol) of acetone were added dropwise at about 25° within 30 minutes and subsequently the mixture was stirred at 35–40° for a further 1 hour. The reaction mixture was treated with 350 ml of 14.2% sulphuric acid while cooling with an ice bath at <30°. The aqueous phase was separated, extracted with 200 ml of tetrahydrofuran and the organic phases were combined and evaporated at 50° on a rotary evaporator. 110 g of crude 2-(p-fluorophenyl)-3-hydroxy-3-methylbutyric acid were obtained as a dark viscous oil.

b) This oil (in a 1 l round flask fitted with a magnetic stirrer, dropping funnel and thermometer) was treated with 240 g of conc. sulphuric acid within 5–10 minutes while cooling with an ice bath, with the reaction temperature not exceeding 20°. The resulting reaction mixture was stirred at 20° for 45 minutes and then poured into 1 kg of ice/water mixture while stirring well. The pink colored precipitate was filtered off under suction, washed 3 times with 100 ml of water each time and twice with 200 ml of hexane each time and finally taken up in 500 ml of methanol while heating to 50°. The pink colored solution obtained was stirred at 50° with 8 g of decolorizing charcoal for 30 minutes, filtered and concentrated. The solid residue was suspended in 500 ml of hexane at 50°, filtered off under suction after cooling to RT, washed twice with 50 ml of hexane each time and dried at 1 mbar for 1 hour. There were obtained 88.0 g of 2-(p-fluorophenyl)-3-methylcrotonic acid as a white powder of m.p. 124–126°; GC purity 99.8 area %;

yield 95.7% based on p-fluorophenylacetic acid.

EXAMPLE 2

Preparation of 2-(p-fluorophenyl)-3-methylcrotonic acid with crystallization of the 2-(p-fluorophenyl)-3-hydroxy-3-methyl-butyric acid intermediate a) A solution of 2-(p-fluorophenyl)-3-hydroxy-3-methylbutyric acid (ex 0.473 mol of p-fluorophenylacetic acid) in tetrahydrofuran, obtained from a reaction carried out analogously to Example 1 a), was dried over $MgSO_4$, filtered and evaporated. The viscous residue was dissolved in 100 ml of toluene at 50° and the solution was stirred with decolorizing charcoal at 50° for 15 minutes, filtered and concentrated at 50° on a rotary evaporator. After distilling off about 30 ml of toluene the residue was treated with 300 ml of hexane at 50°. After cooling, finally in an ice bath, the crystallizate was filtered off under suction, washed twice with 50 ml of hexane each time and then dried at 15 Torr/80° for 1 hour. There were obtained 97.0 g (96.5%) of 2-(p-fluorophenyl)-3-hydroxy-3-methylbutyric acid as white crystals of m.p. 86–88°; GC purity 98%.

b) A solution of 96.5 g of 2-(p-fluorophenyl)-3-hydroxy-3-methylbutyric acid in 200 ml of $CH_2Cl_2$ was cooled in an ice bath and then treated dropwise with 240 g of conc. sulphuric acid within 30 minutes, with the temperature being held at $\leq 20°$. The $CH_2Cl_2$ was then removed to 20° on a rotary evaporator. The yellowish solution was stirred at 20° for a further 45 minutes and then poured into 1 kg of ice/water mixture while stirring well. The white precipitate was filtered off under suction, washed 3 times with 100 ml of water each time and twice with 100 ml of hexane each time and finally dried in a drying oven at 40° for 16 hours and at 100° for 2 hours. There were obtained 87.5 g of 2-(p-fluorophenyl)-3-methylcrotonic acid as a white powder of m.p. 124–126°; GC purity 99.9%; yield 95.6% based on p-fluorophenylacetic acid.

For further purification, 76.7 g of this material were dissolved in 300 ml of $CH_2Cl_2$ at 50°. The solution was treated with 5 g of magnesium sulphate and 2 g of decolorizing charcoal, stirred and, after cooling, filtered. The colorless filtrate was concentrated at 50° on a rotary evaporator under argon. After distillation of about 300 ml of $CH_2CL_2$ the residue was treated with 100 ml of hexane at 50°, a further 75 ml of solvent were distilled off and the mixture was again treated with 75 ml of hexane. After cooling, finally in an ice bath, the crystallizate was filtered off under suction, washed twice with 50 ml of hexane each time and dried at 50° in a drying oven for 1 hour. There were obtained 75.4 g of 2-(p-fluorophenyl)-3-methylcrotonic acid as a white powder of m.p. 124–126°; GC purity 99.95%. The crystallization yield was 98.3%, the total yield was 97% based on 2-(p-fluorophenyl)-3-hydroxy-3-methylbutyric acid and 94% based on p-fluorophenylacetic acid.

EXAMPLE 3
Ethylmagnesium chloride as the base 70.0 g (0.454 mol) of p-fluorophenylacetic acid were reacted with ethylmagnesium chloride as the base in analogy to Example 1 a). 104 g of crude 2-(p-fluorophenyl)-3-hydroxy-3-methylbutyric acid were obtained as a dark oil.

EXAMPLE 4
Methylmagnesium chloride as the base 52.5 g (0.34 mol) of p-fluorophenylacetic acid were reacted with methylmagnesium chloride as the base in analogy to Example 1 a). 63.6 g of crude 2-(p-fluorophenyl)-3-hydroxy-3-methylbutyric acid were obtained as a dark oil.

EXAMPLE 5
Dehydration with polyphosphoric acid 90 g of polyphosphoric acid were placed in a 350 ml sulphonation flask. Then, it was treated dropwise with a solution of 10.0 g (47 mmol) of 2-(p-fluorophenyl)-3-hydroxy-3-methylbutyric acid in 70 ml of $CH_2CL_2$ at 20–25°. The viscous, yellow colored mixture was stirred for 2 hours, with the temperature rising to 35°. After hydrolysis with ice-water the mixture was left to stand overnight and then treated with ether. The organic phase was separated, washed 3 times with water, dried over $MgSO_4$, filtered and the filtrate was concentrated. The residue was dissolved in $CH_2CL_2$ and the solution was treated with hexane and concentrated on a rotary evaporator until crystallization occurred. After standing at RT for 1 hour the crystals were filtered off under suction and washed with cold hexane. There were obtained 67 g (73%) of 2-(p-fluorophenyl)-3-methylcrotonic acid as a white powder.

EXAMPLE 6
Preparation of 2-(p-chlorophenyl)-3-methylcrotonic acid a) 2-(p-Chlorophenyl)-3-hydroxy-3-methylbutyric acid. —24.3 g (1.00 mol) of magnesium shavings were suspended in 50 ml of tetrahydrofuran under argon and while stirring in a 1.5 l four-necked necked flask fitted with a reflux condenser, mechanical stirrer, 500 ml dropping funnel, thermometer and a device for inert gasification. After the dropwise addition of 0.5 ml of 1,2-dibromoethane a solution of 86.4 g (1.10 mol) of isopropyl chloride in 225 ml of tetrahydrofuran was added dropwise within 90 minutes, with the reaction temperature being held at 30–35°. The dark grey suspension obtained was stirred at RT for a further 18 hours. Then, a solution of 80.6 g (0.473 mol) of p- chlorophenylacetic acid in 150 ml of tetrahydrofuran was added dropwise within 1 hour, with the reaction temperature not exceeding 25°. The viscous yellowish suspension obtained was heated to 35° for a further 1 hour. Then, 30.0g (0.516 mol) of acetone were added dropwise at 25° within 30 minutes and the mixture was subsequently heated to 35° for a further 1 hour. The reaction mixture was treated with 350 ml of 14.2% sulphuric acid while cooling with an ice bath at <30°. The organic phase was separated, the aqueous phase was extracted with 100 ml of tetrahydrofuran and the combined organic extracts were evaporated to dryness at 50° on a rotary evaporator. There were obtained 120.9g of crude 2-(p-chlorophenyl)-3-hydroxy-3-methylbutyric acid as a crude oil. An analytical sample was obtained by crystallization from EtOH/ water 1:2 as white crystals; m.p. 65°.

b) 2-(p-Chlorophenyl)-3-methylcrotonic acid. — The 120.9 g of crude 2-(p-chlorophenyl)-3-hydroxy-3-methylbutyric acid obtained above were dissolved in 200 ml of $CH_2Cl_2$ in a 1 l round flask fitted with a magnetic stirrer, thermometer and dropping funnel. The solution was treated with 240 g of conc. sulphuric acid while cooling with an ice bath, with the reaction temperature not exceeding 20°. The $CH_2CL_2$ was then removed at 20° on a rotary evaporator. The residual dark oil was stirred at 50° for a further 30 minutes and then poured on to 1 kg of ice while stirring well. The pink colored precipitate was filtered off under suction, washed 3 times with 100 ml of water each time and taken up in 400 ml of $CH_2CL_2$. The solution was stirred with 20 g of magnesium sulphate and 1 g of decolorizing charcoal and filtered over 200 g of Speedex, with rinsing being carried out with 100 ml of $CH_2CL_2$. The filtrate was concentrated on a rotary evaporator. After distilling off about 250 ml of solvent the residue was treated with 250 ml of hexane. This procedure was repeated twice, with crystallization occurring. The crystals were filtered off under suction, rinsed with 100 ml of hexane and dried at 0.1 mbar. There were obtained 76.3 g of 2-(p-chlorophenyl)-3-methylcrotonic acid as white crystals of m.p. 144–145°; yield 76.6% based on p-chlorophenylacetic acid.

EXAMPLE 7
7.1. Asymmetric hydrogenation of 2-(p-fluorophenyl)-3-methylcrotonic acid a) Ruthenium-catalyzed hydrogenation. — A catalyst solution was prepared in a glove box ($O_2$ content <1 ppm)

by dissolving 0.418 g (0.544 mmol) of Ru(OAc)$_2$[(R)-BIPHEMP] in 100 ml of methanol and stirring at RT for 10 minutes. Then, 211.2 g (1.0875 mol) of 2-(p-fluorophenyl)-3-methylcrotonic acid and 700 ml of methanol were placed in a 2 l autoclave and the catalyst solution prepared above was added. The autoclave was sealed and the hydrogenation was carried out while stirring at 10° and under a pressure of 150–180 bar. The conversion was 100% after 24 hours. The hydrogenation solution was evaporated at 50°/200 mbar and the residue was distilled at 108–110°/0.01 mbar. There were obtained 208.1 g (97.5%) of (S)-2-(p-fluorophenyl)-3-methylbutyric acid as a colorless oil which solidified at RT; m.p. 53–56°; 96.6% ee.

b) A catalyst solution was prepared in a glove box (O$_2$ content <1 ppm) at RT by dissolving 0.124 g (0.155 mmol) of Ru(OAc)2[(R)-MeOBIPHEP] in 50 ml of methanol. Then, 30.0 g (154.5 mmol) of 2-(p-fluorophenyl)-3-methylcrotonic acid and 38 ml of methanol were placed in a 185 ml autoclave and the catalyst solution prepared above was added. The autoclave was sealed and the hydrogenation was carried out at 20° while stirring and under a constant pressure of 180 bar. The conversion was 100% after 6 hours. The hydrogenation solution was evaporated at 50°/20 mbar and the residue was distilled in a bulb tube oven at 125°/0.2 mbar. There were obtained 28.04 g (92.5%) of (S)-2-(p-fluorophenyl)-3-methylbutyric acid as a colorless oil which crystallized out at RT; chemical purity 99.9 GC area %; 90% ee.

c) 1.0 g (5.15 mmol) of 2-(p-fluorophenyl)-3-methylcrotonic acid and 0.52 g (5.15 mmol) of triethylamine were suspended in 6 ml of methanol in a glove box (O$_2$ content <1 ppm) in a 30 ml autoclave at RT and a solution of 4.1 mg (0.0051 mmol) of Ru(OAc)$_2$-((R)-MeOPIPHEP) in 5 ml of methanol was added as the catalyst. The autoclave was sealed and the hydrogenation was carried out at 20° while stirring and under an initial pressure of 200 bar. The pressure decreased to about 190 bar during the reaction. After a reaction period of 21 hours a sample of the hydrogenation solution was evaporated at 50°/20 mbar and analyzed. There was obtained (S)-2-(p-fluorophenyl)-3-methylbutanoic acid with an ee of 93%.

d)-l) Hydrogenations were carried out in a manner analogous to Example c) with the addition of the bases listed in Table 1:

TABLE 1

| Example | Base | Conversion [%] | ee [%] (S) |
|---|---|---|---|
| 7.1.d) | Tributylamine | 100 | 93 |
| 7.1.e) | Diethylamine | 100 | 93 |
| 7.1.f) | (R)-1-Phenyl-ethylamine | 70 | 92 |
| 7.1.g) | (S)-1-Phenyl-ethylamine | 93 | 92 |
| 7.1.h) | Pyrrolidine | 100 | 93 |
| 7.1.i) | Diisopropylamine | 100 | 93 |
| 7.1.j) | N-Ethyldiisopropylamine | 100 | 92 |
| 7.1.k) | Ethanolamine | 50 | 92 |
| 7.1.l) | 25 per cent NH$_4$OH solution | 100 | 91 | m) Rhodium-catalyzed hydrogenation. —A catalyst solution was prepared in a glove box (O$_2$ content <1 ppm) by dissolving 0.01045 g (0.0257 mmol) of [Rh(COD)$_2$]BF$_4$ and 0.01861 g (0.0257 mmol) of (R,S)-BPPFA-EPIP in 20 ml of tetrahydrofuran and stirring at RT for 15 minutes. Then, 5.0 g (25.75 mmol) of 2-(p-fluorophenyl)-3-methylcrotonic acid, 13 ml of methanol and 33 ml of tetrahydrofuran were placed in a 185 ml autoclave and the catalyst solution prepared above was added. The autoclave was sealed and the hydrogenation was carried out at 20° while stirring and under a constant pressure of 50 bar. The conversion was 100% after 24 hours. The hydrogenation solution was evaporated at 50°/200 mbar and the residue was distilled at 108–110°/0.01 mbar. There were obtained 4.8 g (97%) of (S)-2-(p-fluorophenyl)-3-methylbutyric acid as a colorless oil which solidified at RT; 98.2% ee.

7.2. Asymmetric hydrogenation of 2-(p-chlorophenyl)-3-methylcrotonic acid a) Ruthenium-catalyzed hydrogenation. — A catalyst solution was prepared in a glove box (O$_2$ content <1 ppm) by dissolving 0.0914 g (0.119 mmol) of Ru(OAc)$_2$[(S)-BIPHEMP] in 50 ml of methanol and stirring at 20° for 15 minutes. Then, 5.0 g (23.74 mmol) of 2-(p- chlorophenyl)-3-methylcrotonic acid and 23 ml of methanol were placed in a 185 ml autoclave and the catalyst solution prepared above was added. The autoclave was sealed and the hydrogenation was carried out at 20° while stirring and under a constant pressure of 60 bar. The conversion was 100% after 4 hours. The hydrogenation solution was evaporated at 50°/20 mbar and the residue was distilled in a bulb tube oven at 150°/0.2 mbar. There were obtained 4.6 g (92%) of (R)-2-(p-chlorophenyl)-3-methylbutyric acid as a colorless oil which crystallized out at RT; chemical purity 98.8 area %; 90.5% ee; [α]$_{589}$=−42.3° (c=1, methanol).

b) Rhodium-catalyzed hydrogenation. —A catalyst solution was prepared in a glove box (O$_2$ content <1 ppm) by dissolving 0.0482 g (0.1 19 mmol) of [Rh(COD)$_2$]BF$_4$ and 0.0858 g (0.1 19 mmol) of (R,S)-BPPFA-EPIP in 20 ml of tetrahydrofuran and stirring at 20° for 15 minutes. Then, 5.0 g (23.74 mmol) of 2-(p-chlorophenyl)-3-methylcrotonic acid, 13 ml of methanol, 33 ml of tetrahydrofuran were placed in a 185 ml autoclave and the catalyst solution prepared above was added. The autoclave was sealed and the hydrogenation was carried out at 20° while stirring and under a constant pressure of 50 bar. The conversion was 100% after 18 hours. The hydrogenation solution was evaporated at 50°/20 mbar and the residue was distilled in a bulb tube oven at 150°/0.2 mbar. There were obtained 4.8 g (96%) of (S)-2-(p-chlorophenyl)-3-methylbutyric acid as a colorless oil which crystallized out at RT; chemical purity 99.9 GC area %; 97.6% ee.

We claim:

1. A process for making a compound of formula I

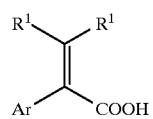

I wherein R$^1$ signifies C$_1$–C$_5$-alkyl; and Ar signifies an aryl group which is optionally substituted by one or more substituents selected from the group consisting of halogen, phenyl, C$_1$–C$_5$-alkyl, C$_1$–C$_5$-alkoxy, perfluorinated C$_1$–C$_5$-alkyl and pertluorinated C$_1$–C$_5$-alkoxy, comprising (a) dehydrating a compound of formula III

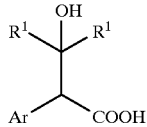   III wherein $R^1$ and Ar as set forth above, in the presence of a strong acid selected from concentrated sulphuric acid or concentrated polyphosphoric acid at a temperature of from about 0 to about 40° C.; and (b) recovering the compound of formula I.

2. The process of claim 1, wherein the dehydrating of (a) further takes place in the presence of a solubilizer.

3. The process of claim 2 wherein the solubilizer is selected from methylene chloride, dioxane, or acetic acid.

4. The process of claim 1, wherein Ar signifies a phenyl group substituted by fluorine, chlorine, bromine, methyl, methoxy or trifluoromethoxy.

5. The process of claim 4 wherein the strong acid is concentrated sulphuric acid.

6. The process of claim 5 wherein the temperature of (a) is from about 20 to about 25° C.

7. The process of claim, 5 wherein Ar is selected from p-fluorophenyl and p-chlorophenyl.

8. The process of claim 4 wherein the strong acid is concentrated polyphosphoric acid.

9. The process of claim 8 wherein the temperature of (a) is from about 20 to about 35° C.

10. The process of claim 4 wherein Ar is selected from p-fluorophenyl and p-chlorophenyl.

11. A compound of the formula

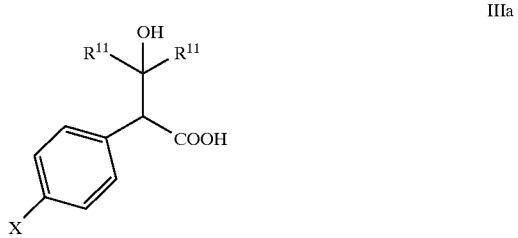   IIIa wherein $R^{11}$ signifies methyl or ethyl; and X signifies fluorine, chlorine or bromine.

* * * * *